United States Patent [19]

Suzuki

[11] Patent Number: 4,634,650
[45] Date of Patent: Jan. 6, 1987

[54] TONER FOR DEVELOPING LATENT ELECTROSTATIC IMAGES, CONTAINING CHARGE CONTROL AGENT

[75] Inventor: Tetsuro Suzuki, Fuji, Japan

[73] Assignee: Ricoh Company, Ltd., Tokyo, Japan

[21] Appl. No.: 759,324

[22] Filed: Jul. 26, 1985

[30] Foreign Application Priority Data

Jul. 31, 1984 [JP] Japan .................. 59-158679

[51] Int. Cl.$^4$ .............................................. G03G 9/08
[52] U.S. Cl. ...................................... 430/110; 430/903
[58] Field of Search ............................... 430/110, 903

[56] References Cited

U.S. PATENT DOCUMENTS 4,444,862  4/1984  Yagi et al. ............................ 430/67

Primary Examiner—John D. Welsh
Attorney, Agent, or Firm—Oblon, Fisher, Spivak, McClelland & Maier

[57] ABSTRACT

A toner for developing latent electrostatic images comprising particles is disclosed, which is composed of a mixture of a colorant and/or magnetic material, a binder agent and a charge controlling agent of the formula

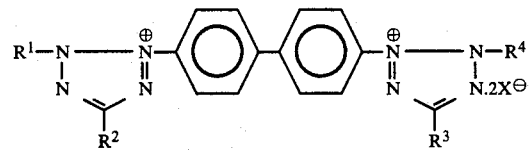

wherein $R^1$, $R^2$, $R^3$ and $R^4$ each represent an unsubstituted or substituted aryl group; and X represents an anionic functional group.

18 Claims, No Drawings

TONER FOR DEVELOPING LATENT ELECTROSTATIC IMAGES, CONTAINING CHARGE CONTROL AGENT

BACKGROUND OF THE INVENTION

The present invention relates to a toner for developing latent electrostatic images in electrophotography, electrostatic recording, electrostatic printing and the like, and more particularly to a toner for use in dry type development in the above technical field.

Generally in a dry-type development method, a developer which is prepared by mixing a fine powder-like toner and a carrier is employed for developing latent electrostatic images. The toner comprises a pigment dispersed in a natural or synthetic resin, and a dye which works as an agent for controlling the electric charge of the toner (hereinafter referred to as a charge controlling agent). The carrier is made of glass beads or iron powder. As the development techniques which belong to the category of dry-type development, there are known, for example, cascade development, fur-brush development, magnetic-brush development, impression development and powder-cloud development.

A conventional toner for use in the dry-type development method is prepared by adding a pigment such as carbon black to a natural or synthetic thermoplastic resin, together with a charge controlling agent, and fusing the mixture, cooling the fused mixture and then finely grinding the mixture to finely-divided particles with a particle size ranging from 5 $\mu$m to 20 $\mu$m.

As charge controlling agents for use in a toner of a dry-type developer, the following charge controlling agents are proposed in Japanese Patent Publication No. 41-2427.

(1) Positive charge controlling agents
   Fettschwarz HBN (C.I. No. 26150),
   Nigrosin (C.I. No. 50415),
   Sudantiefschwarz BB (C.I. No. 26150),
   Brilliantspiritschwarz TN (made by Farbenfabriken Bayer Co., Ltd.)
   Zaponschwarz X (made by Farbwerke Hoechst Co., Ltd.)
(2) Negative charge controlling agents
   Ceresschwarz (R)G (made by Farbenfabriken Bayer, Co., Ltd.)
   Chromogenschwarz ETCO (C.I. No. 14645)
   Azo Oil Black R (made by National Aniline Div. Co., Ltd.)

The above charge control agents are selected from dyes and are complicated in chemical structure, unstable and susceptible to mechanical frictions and shocks, changes in temperature and humidity, electrical shocks and illumination, by which they are easily decomposed and the charge controlling properties thereof are impaired.

Furthermore, many of the conventional charge control agents are extremely difficult to disperse or dissolve uniformly in thermoplastic resins, so that the quantity of electric charges in each toner particle containing such a conventional charge controlling agent becomes different. Therefore, the charge distribution in the toner particles differs from portion to portion of the toner. As a matter of course, such a toner is not capable of developing latent electrostatic images to visible images precisely corresponding to the latent electrostatic images, and if it is used in practice in a development apparatus, the development performance reliability thereof cannot be guaranteed.

SUMMARY OF THE INVENTION

It is therefore an object of the present invention to provide an improved toner for developing latent electrostatic images, from which the above described shortcomings of the conventional toners have been eliminated, in particular, which toner is capable of retaining a sufficiently high quantity of electric charges in each toner particle, with each toner particle being uniformly charged, thereby attaining stable and precise development of electrostatic images.

The above object of the present invention is attained by a toner comprising a mixture of a colorant and/or magnetic material, a binder agent and a charge controlling agent of the formula

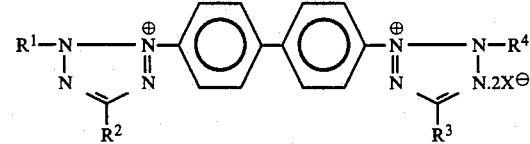

wherein $R^1$, $R^2$, $R^3$ and $R^4$ each represent an unsubstituted or substituted aryl group such as phenyl and naphthyl, and X represents an anionic functional group such as halogen, para-toluenesulfonate, tetra-fluoborate and hexafluorophosphate.

Examples of the substituents of the aryl group are halogen, nitro, alkoxy, carboxyl, cyano, amino, and lower alkyl.

DETAILED DESCRIPTION OF THE PREFERRED EMBODIMENTS

Representative examples of the charge controlling agent of the above formula for use in the present invention are as follows:

(Compound No. 1)

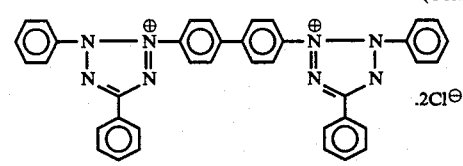

(Compound No. 2)

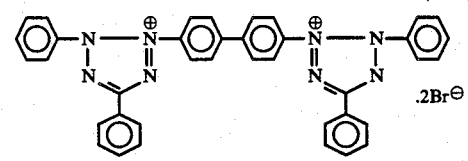

(Compound No. 3)

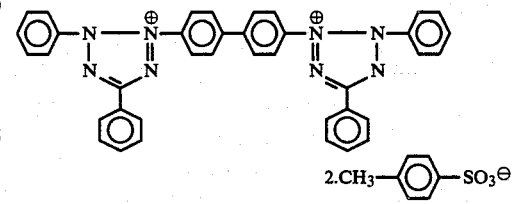

-continued (Compound No. 4) .2BF4⊖

(Compound No. 5) .2I⊖

(Compound No. 6) .2Cl⊖

(Compound No. 7) 2. [naphthol-SO3⊖]

(Compound No. 8) .2Br⊖

(Compound No. 9) 2. [C6H4-SO3⊖]

(Compound No. 10) 2.O2N—[C6H4]—SO3⊖

In the present invention, any of the above described charge controlling agents can be used alone or in combination. It is preferable that the content of the charge controlling agent in the toner be in the range of 0.5 to 7 parts by weight to 100 parts by weight of a binder agent or binder agents contained in the toner.

Furthermore, in the toner according to the present invention, conventional binder agents can be employed. Examples of such binder agents are as follows:

(1) Polymers prepared by polymerizing the following monomers, and copolymers prepared by polymerizing any two or more different monomers of the following monomers, and mixtures of these polymers and copolymers.

styrene and styrene derivatives, such as p-chlorostyrene; vinyl compounds such as vinyl naphthalene, vinyl chloride, vinyl bromide and vinyl fluoride; vinyl esters such as vinyl acetate, vinyl propionate, vinyl benzoate, vinyl butyrate; α-methylene aliphatic monocarboxylic acid esters such as methyl acrylate, ethyl acrylate, n-butyl acrylate, isobutyl acrylate, dodecyl acrylate, n-octyl acrylate, ethyl 2-chloroacrylate, phenyl acrylate, methyl αchloro acrylate, methyl methacrylate, ethyl methacrylate, butyl methacrylate; acrylonitrile, methacrylonitrile, acrylic amide; vinyl ethers such as vinyl methyl ether, vinyl isobutyl ether, vinyl ethyl ether; vinyl ketones such as vinyl methyl ketone, vinyl hexyl ketone; and N-vinyl compounds such as N-vinylpyrrole, N-vinylcarbazole, N-vinylindole and N-vinylpyrrolidone.

(2) Non-vinyl-type thermoplastic resins such as rosin-modified phenol-formaldehyde resin, oil-modified epoxy resin, polyurethane, cellulose resin, polyether resin; and mixtures of such non-vinyl-type thermoplastic resins and the above-mentioned vinyl-type resins.

In order to make the toner pressure-fixable, the following resins can be employed:

Polyolefins (low molecular weight polyethylene, low mclecular weight polypropylene, polyethylene oxide, polytetrafluoroethylene), epoxy resin, polyester resin (the acid value thereof being 10 or less), styrene-butadiene copolymer (the monomer ratio thereof being 5~30: 95~70), olefin copolymers (ethylene - acrylic acid copolymer, ethylene - acrylic acid ester copolymer, ethylene - methacrylic acid copolymer, ethylene - methacrylic acid ester copolymer, ethylene - vinyl chloride copolymer, ethylene - vinyl acetate copolymer, ionomer resin), polyvinyl - pyrrolidone, methylvinyl ether - maleic anhydride copolymer, maleic-acid-modified phenolic resin, and phenol-modified-terpene resin.

To the toner according to the present invention, there can be further added a coloring agent such as a pigment or a dye when necessary. As the coloring agent, the following conventional coloring agents can be employed:

Carbon black, nigrosine dye, Aniline Blue, Calconyl Blue, Chrome Yellow, Ultramarine Blue, Du Pont Oil Red, Quinoline Yellow, Methylene Blue Chloride, Phthalocyanine Blue, Malachite Green Oxalate, Lamp Black, Oil Black, Azo Oil Black, Rose Bengale and mixtures of the above coloring agents.

To the toner according to the present invention, there can be added a magnetic material so as to make the toner magnetic. When a magnetic material serves as colorant, addition of another colorant to the toner can be omitted.

As the magnetic material to be contained in the toner according to the present invention, a material which is chemically stable and in the form of fine particles with a particle size of 3 μm or less, for example, magnetite, is preferable. Representative examples of each magnetic materials that can be used in the present invention are as follows:

Metals such as cobalt, iron, nickel, alloys or mixtures of aluminum, cobalt, copper, iron, lead, magnesium, nickel, tin, zinc, antimony, beryllium, bismuth, cadmium, calcium, manganese, selenium, titanium, tungsten or vanadium; metal compounds containing metal oxides such as aluminum oxide, iron oxide, copper oxide, nickel oxide, zinc oxide, titanium oxide or magnesium oxide; refractory nitrides such as vanadium nitride and chrominum nitride; and carbides such as tungsten carbide and silica carbide; ferrite; and mixtures of the above-mentioned materials.

It is preferable that the average particle size of the above-mentioned ferromagnetic materials be in the range of about 0.1 μm to 3 μm and the amount of the ferromagnetic material contained in the toner be in the range of about 50 parts by weight to about 300 parts by weight with respect to 100 parts by weight of the resin components, more preferably in the range of 90 parts by weight to 200 parts by weight with respect to 100 parts by weight of the resin component.

The toner according to the present invention can be used as a one-component-type developer. It can also be used as a non-magnetic toner in combination with a conventional carrier, thereby constituting a two-component type developer. Either in the case of a one-component-type or in the case of a two-component-type developer, the toner according to the present invention can be used in combination with a fluidizing agent if necessary. As the fluidizing agent, for instance, hydrophobic silica, titanium oxide and aluminum oxide can be used in the form of finely ground particles. It is preferable that the amount of such fluidizing agent be in the range of 0.1 to 1 part by weight with respect to 100 parts by weight of the toner.

A procedure of developing latent electrostatic images, for example, in electrophotography, by use of a developer containing the toner according to the present invention, will now be explained. In the development procedure, any kind of photoconductors can be employed, for example, a selenium photoconductor; a selenium-tellurium-alloy photoconductor; a photoconductor comprising an electroconductive support material, an intermediate layer consisting essentially of an ammonia-treated casein, formed on the electroconductive support material, and a photosensitive layer formed on the intermediate layer, which photosensitive layer comprises an inorganic photoconductive material such as zinc oxide, cadmium oxide, cadmium selenide, cadmium selenide oxide, lead oxide or mercury sulfide, dispersed in a binder resin; and a photoconductor comprising an electroconductive support material, an intermediate layer comprising casein and a water-soluble polymeric material formed on the electroconductive support material, and a photosensitive layer which is formed on the intermediate layer and comprises an organic photoconductive material such as anthracene, anthrone or poly-N-vinylcarbazole which is dispersed in a binder resin.

To the surface of a photosensitive layer of any of the above-mentioned photoconductors, electric charges are applied uniformly by corona charging by use of, for example, a corotron or a scorotron, whereby the entire surface of the photosensitive layer is uniformly charged. The thus uniformly charged photosensitive layer is exposed to light images, so that latent electrostatic images corresponding to the light images are formed on the surface of the photosensitive layer. The latent electrostatic images are then developed, to the corresponding visible toner images, for example, by a magnetic brush development method, with a developer containing the toner according to the present invention. The thus formed toner images are then transferred to a transfer sheet under application of corona charges or by adhesion image transfer. The transferred toner images are then fixed to the transfer sheet, for example, by a heat plate image fixing method, a heat roller image fixing method or a pressure application image fixing method or a flash-light application image fixing method. The above described procedure can be also applied to electrostatic recording.

Embodiments of a toner according to the present invention will now be explained in detail by referring to the following specific examples:

EXAMPLE 1

A mixture of the following components was kneaded under application of heat thereto by heat rollers:

|  | Parts by Weight |
| --- | --- |
| Polystyrene | 100 |
| Carbon black | 10 |
| Charge Controlling Agent (Compound No. 1) | 2 |
| Magnetite (average particle size: 0.1 μm) | 100 |

After the mixture was cooled, it was ground to small particles, whereby a magnetic toner with an average volume particle size of 12 μm and an electric resistivity of $4 \times 10^{12}$ Ωcm, according to the present invention, was prepared.

A zinc oxide photoconductor was uniformly charged to a negative polarity under application of corona charge of −6KV in the dark. The thus negatively charged zinc oxide photoconductor was exposed to light images, so that latent electrostatic images were formed on the photoconductor. The latent electrostatic images were then developed with the above prepared magnetic toner by use of a magnetic brush development apparatus. The developed toner images were transferred to a transfer sheet of plain paper under application thereto of negative electric charges and were then fixed thereto under application of heat, whereby clear copy images with high density were obtained on the transfer sheet.

EXAMPLE 2

A mixture of the following components were kneaded under application of heat by heat rollers:

|  | Parts by Weight |
| --- | --- |
| Polyester resin | 100 |
| Carbon black | 10 |
| Charge controlling agent (Compound No. 2) | 2 |

After the mixture was cooled, it was finally ground, so that a non-magnetic toner with an average volume particle size of 12 μm according to the present invention was obtained.

3 parts by weight of the thus prepared non-magnetic toner were mixed with 100 parts by weight of an iron powder carrier, whereby a two-component-type developer was prepared.

An organic photoconductor comprising polyvinylcarbazole and trinitrofluorenone (hereinafter referred to as the PVK-TNF photoconductor) was uniformly charged to a negative polarity under application of corona charge of −6KV in the dark. The thus negatively charged PVK-TNF photoconductor was exposed to light images, so that latent electrostatic images were formed on the photoconductor.

The latent electrostatic images were then developed with the above prepared two-component-type developer by use of a magnetic brush development apparatus. The thus developed toner images were then transferred from the photoconductor to a transfer sheet of plain paper, whereby clear copy images with high density were obtained on the transfer sheet. This copying process was repeated 100,000 times. The result was that clear copy images were obtained throughout the copying process of making 100,000 copies.

EXAMPLE 3

A mixture of the following components were kneaded under application of heat by heat rollers:

|  | Parts by Weight |
| --- | --- |
| Epoxy resin | 100 |
| Charge controlling agent (Compound No. 3) | 3 |
| Magnetite (average particle size: 0.1 μm) | 100 |

After the mixture was cooled, it was finally ground, so that a magnetic toner with an average volume particle size of 12 μm was obtained, which was employed as a one-component type developer.

A PVK-TNF photoconductor was uniformly charged to a negative polarity under application of corona charge of −6KV in the dark. The thus negatively charged PVK-TNF photoconductor was exposed to light images, so that latent electrostatic images were formed on the photoconductor.

The latent electrostatic images were developed with the above prepared one-component-type developer by use of a magnetic brush development apparatus. The thus developed toner images were then transferred from the photoconductor to a transfer sheet of plain paper, whereby clear copy images with high density were obtained on the transfer sheet. This copying process was repeated 100,000 times. The result was that clear copy images were obtained throughout the copying process of making 100,000 copies.

EXAMPLE 4

A mixture of the following components was kneaded under application of heat thereto by heat rollers:

|  | Parts by Weight |
| --- | --- |
| Styrene-butylmethacrylate copolymer | 100 |
| Carbon black | 10 |
| Charge Controlling Agent (Compound No. 4) | 3 |

After the mixture was cooled, it was ground to small particles, whereby a non-magnetic toner with an average volume particle size of 12 m was obtained.

3 parts by weight of the thus prepared non-magnetic toner were mixed with 100 parts by weight iron powder carrier, whereby a two-component-type developer was prepared.

A zinc oxide photoconductor was uniformly charged to a negative polarity under application of corona charge of −6KV in the dark. The thus negatively charged zinc oxide photoconductor was exposed to light images, so that latent electrostatic images were formed on the photoconductor. The latent electrostatic images were then developed with the above prepared two-component-type developer by use of a magnetic brush development apparatus. The developed toner images were transferred to a transfer sheet of plain paper under application thereto of negative electric charges and were then fixed thereto under application of heat, whereby clear copy images with high density were obtained on the transfer sheet.

This copying process was repeated 100,000 times. The result was that clear copy images were obtained throughout the copying process of making 100,000 copies.

What is claimed is:

1. A toner for developing latent electrostatic images consisting essentially of particles of a mixture of a colorant, a binder agent and a charge controlling agent in a charge controlling effective amount of the formula

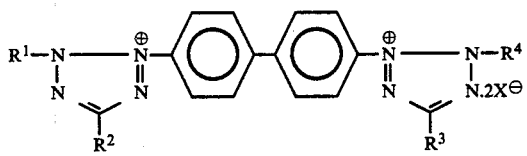

wherein $R^1$, $R^2$, $R^3$ and $R^4$ each represent an unsubstituted or substituted aryl group; and X represents an anionic functional group.

2. A toner for developing latent electrostatic images as claimed in claim 1, wherein said aryl group is phenyl.

3. A toner for developing latent electrostatic images as claimed in claim 1, wherein said aryl group is naphthyl.

4. A toner for developing latent electrostatic images as claimed in claim 1, wherein the substituent of said aryl group is selected from the group consisting of halogen, nitro, alkoxy, carboxyl, cyano, amino and lower alkyl.

5. A toner for developing latent electrostatic images as claimed in claim 1, wherein said anionic functional group is selected from the group consisting of halogen, paratoluenesulfonate, tetra-fluoborate and hexafluorophosphate.

6. A toner for developing latent electrostatic images as claimed in claim 1, wherein the content of said charge controlling agent in said toner is in the range of 0.5 to 7 parts by weight to 100 parts by weight of said binder agent.

7. A toner for developing latent electrostatic images as claimed in claim 1, wherein said binder agent is selected from the group consisting of:
(1) polymers and copolymers of the following monomers, and mixtures of the polymers and copolymers: styrene and styrene derivatives, vinyl naphthalene, vinyl chloride, vinyl bromide, vinyl fluoride, vinyl esters, α-methylene aliphatic monocarboxylic acid esters, acrylonitrile, methacrylonitrile, acrylic amide, vinyl ethers, vinyl ketones, and N-vinyl compounds, (2) non-vinyl-type thermoplastic resins, and
(3) mixtures of the first mentioned polymers or copolymers and the second mentioned non-vinyl-type thermoplastic resins.

8. A toner for developing latent electrostatic images as claimed in claim 1, in which said mixture further comprises a magnetic powder-like material.

9. A toner for developing latent electrostatic images as claimed in claim 8, wherein the content of said magnetic powder-like material in said toner is about 50 to about 300 parts by weight with respect to 100 parts by weight of said binder agent.

10. A toner for developing latent electrostatic images consisting essentially of particles of a mixture of a powder of a magnetic material in an amount effective to render the composition magnetic, a binder agent and a charge controlling agent in a charge controlling effective amount of the formula

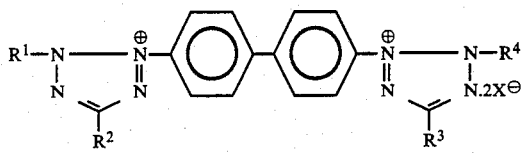

wherein $R^1$, $R^2$, $R^3$ and $R^4$ each represent an unsubstituted or substituted aryl group; and X represents an anionic functional group.

11. A toner for developing latent electrostatic images as claimed in claim 10, wherein said aryl group is phenyl.

12. A toner for developing latent electrostatic images as claimed in claim 10, wherein said aryl group is naphthyl.

13. A toner for developing latent electrostatic images as claimed in claim 10, wherein the substituent of said aryl group is selected from the group consisting of halogen, nitro, alkoxy, carboxyl, cyano, amino and lower alkyl.

14. A toner for developing latent electrostatic images as claimed in claim 10, wherein said anionic functional group is selected from the group consisting of halogen, para-toluenesulfonate, tetra-fluoborate and hexafluorophosphate.

15. A toner for developing latent electrostatic images as claimed in claim 10, wherein the content of said charge controlling agent in said toner is in the range of 0.5 to 7 parts by weight to 100 parts by weight of said binder agent.

16. A toner for developing latent electrostatic images as claimed in claim 10, wherein said binder agent is selected from the group consisting of:
(1) polymers and copolymers of the following monomers, and mixtures of the polymers and copolymers: styrene and styrene derivatives, vinyl naphthalene, vinyl chloride, vinyl bromide, vinyl fluoride, vinyl esters, α-methylene aliphatic monocarboxylic acid esters, acrylonitrile, methacrylonitrile, acrylic amide, vinyl ethers, vinyl ketones, and N-vinyl compounds,
(2) non-vinyl-type thermoplastic resins, and
(3) mixtures of the first mentioned polymers or copolymers and the second mentioned non-vinyl-type thermoplastic resins.

17. A toner for developing latent electrostatic images as claimed in claim 10, in which said mixture further comprises a pigment or dye.

18. A toner for developing latent electrostatic images as claimed in claim 10, wherein the content of said magnetic powder-like material in said toner is about 50 to about 300 parts by weight with respect to 100 parts by weight of said binder agent and the particle size of said magnetic material is about 0.1 to 3.0 micrometers.

* * * * *